United States Patent [19]

Ohsaka et al.

[11] 4,091,043
[45] May 23, 1978

[54] PROCESS FOR THE PREPARATION OF 1-CHLORO-1,1-DIFLUOROETHANE AND/OR 1,1,1-TRIFLUOROETHANE

[75] Inventors: Yohnosuke Ohsaka, Takatsuki; Osamu Morimoto, Daito, both of Japan

[73] Assignee: Daikin Kogyo Co., Ltd., Osaka, Japan

[21] Appl. No.: 752,926

[22] Filed: Dec. 21, 1976

[30] Foreign Application Priority Data

Dec. 29, 1975 Japan .................................. 51-157371

[51] Int. Cl.² ............................................ C07C 19/08
[52] U.S. Cl. ................................................ 260/653.7
[58] Field of Search ................................... 260/653.7

[56] References Cited
U.S. PATENT DOCUMENTS 2,005,710  6/1935  Dandt et al. ...................... 260/653.7

Primary Examiner—C. Davis
Attorney, Agent, or Firm—Lane, Aitken, Dunner & Ziems

[57] ABSTRACT

A process for preparing 1-chloro-1,1-difluoroethane and/or 1,1,1-trifluoroethane by fluorination of 1,1,1-trichloroethane with anhydrous hydrofluoric acid in the presence of antimony pentachloride in a halogenated hydrocarbon solvent which is capable of dissolving both the catalyst and 1,1,1-trichloroethane, is substantially inert in the reaction system and which has a boiling point of above 0° C and a melting point of below 60° C. By varying the mole ratio of hydrofluoric acid to 1,1,1-trichloroethane both fed together into a solution of the catalyst in the solvent, 1-chloro-1,1-difluoroethane and 1,1,1-trifluoroethane are obtained with a variety of desired ratios.

15 Claims, 1 Drawing Figure

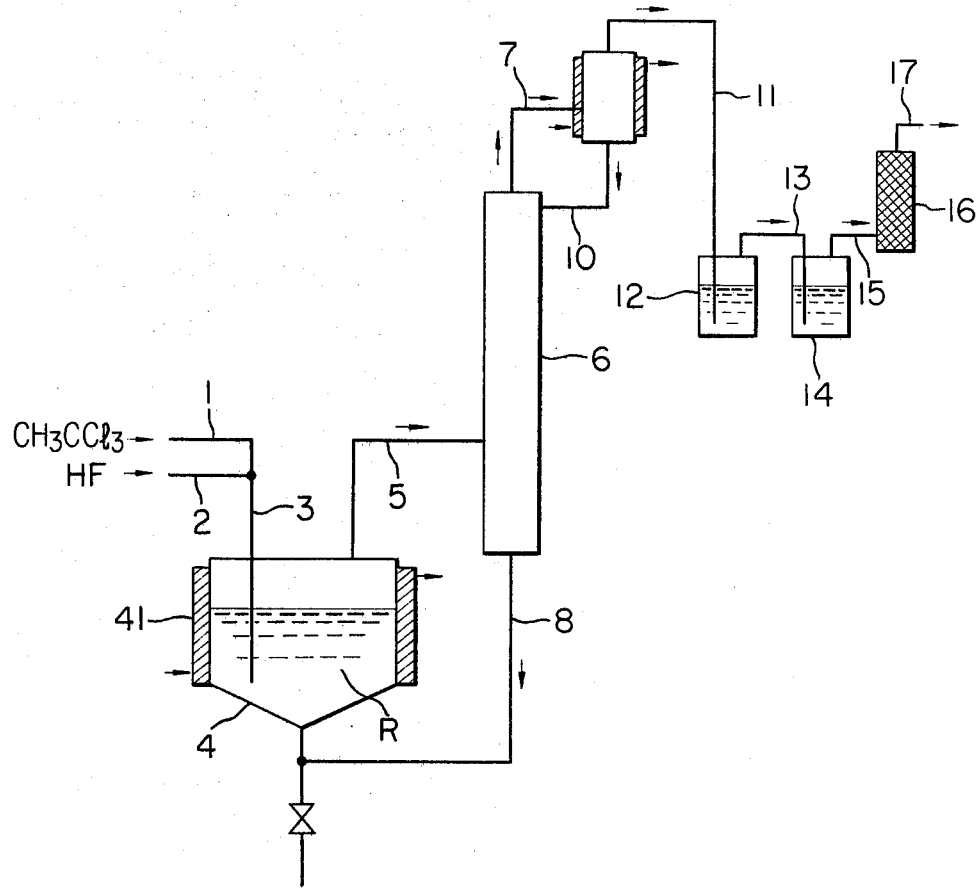

PROCESS FOR THE PREPARATION OF 1-CHLORO-1,1-DIFLUOROETHANE AND/OR 1,1,1-TRIFLUOROETHANE

BACKGROUND OF THE INVENTION

This invention relates to a process for preparing 1-chloro-1,1-difluoroethane and/or 1,1,1-trifluoroethane by fluorination of 1,1,1-trichloroethane with anhydrous hydrofluoric acid in the presence of antimony pentachloride.

1-Chloro-1,1-difluoroethane (hereinafter referred to simply as F-142$b$) is known to be important as a material for the production of vinylidene fluoride. 1,1,1-Trifluoroethane (hereinafter referred to simply as F-143$a$) as well as F-142$b$ is useful as a refrigerant and a propellant in the aerosols industries.

It is well known that F-142$b$ and F-143$a$ are obtained by fluorination of 1,1,1-trichloroethane (generally called as methylchloroform) with the anhydrous hydrofluoric acid in the presence of antimony pentachloride. Known processes are, however, intended to prepare either F-142$b$ or F-143$a$ alone rather than to produce the both compounds in an arbitrary ratio. Needless to say, it has been often experienced that even if either of the compounds is intended to be produced, the formation of the other inevitably results since methylchloroform successively undergoes the following reactions:

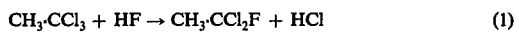
$$CH_3 \cdot CCl_3 + HF \rightarrow CH_3 \cdot CCl_2F + HCl \quad (1)$$

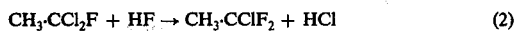
$$CH_3 \cdot CCl_2F + HF \rightarrow CH_3 \cdot CClF_2 + HCl \quad (2)$$

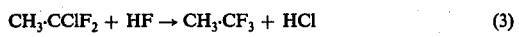
$$CH_3 \cdot CClF_2 + HF \rightarrow CH_3 \cdot CF_3 + HCl \quad (3)$$

For example, W. B. Whalley describes, in J. Soc. Chem. Ind. Vol. 66, p. 427 (1946), the production of F-143$a$ in which F-143$a$ is formed by a relatively easy method, but makes no mention of the production of F-142$b$ and F-143$a$ in arbitrary ratios.

Japanese Patent Publication No. 3965/1974 discloses a process for producing F-142$b$, in which selective production of F-142$b$ is successfully attained. But it does not comment upon the production of F-142$b$ and F-143$a$ in arbitrary ratios.

As previously mentioned, both F-142$b$ and F-143$a$ are useful compounds. Accordingly, there exists a need for an industrial process wherein F-142$b$ and F-143$a$ can be produced in a desired ratio according to demand.

In addition, known processes are not satisfactory for the production of F-143$a$ alone. For example, in the process of W. B. Whalley, continuous production of F-143$a$ is difficult. In this process, antimony pentachloride is reacted with anhydrous hydrofluoric acid to obtain a compound having an empirical formula, $SbF_3Cl_2 \cdot 2HF$, which is subsequently reacted with methylchloroform to obtain F-143$a$.

Likewise, known processes are not satisfactory for the production of F-142$b$ alone. For example, in the process as described in the Japanese Patent Publication No. 3965/1974, a reactor equipped with a condenser is used for the production of F-142$b$. In the reactor, methylchloroform and anhydrous hydrofluoric acid are interacted in the presence of antimony pentachloride under a reaction pressure ranging from 0 kg/cm$^2$G to 3.0 kg/cm$^2$G and at a reaction temperature ranging from the boiling point of F-142$b$ to the boiling point of anhydrous hydrofluoric acid at the reaction pressure. In the condenser, the recovery of F-142$b$ from the gas introduced from the reactor is effected at a condenser temperature ranging from a temperature lower by 10° C than the boiling point of F-142$b$ at the reaction pressure to the reaction temperature. However, the resulting F-142$b$ which is taken out from the reaction system disadvantageously contains a substantial amount of anhydrous hydrofluoric acid. It is very difficult to recover the hydrofluoric acid from the product. In addition, removal of anhydrous hydrofluoric acid by passing the F-142$b$ product obtained by the process into water or an aqueous alkaline solution results in a loss of the anhydrous hydrofluoric acid and as well as other useful materials. Moreover, the Japanese Patent Publication proposes to further react the anhydrous hydrofluoric acid-containing F-142$b$ product with methylchloroform in the presence of antimony pentachloride in another reactor. However, this process requires an additional reactor and is thus poor in economy.

SUMMARY OF THE INVENTION

The present invention provides a process for preparing 1-chloro-1,1-difluoroethane and/or 1,1,1-trifluoroethane. The process includes reacting 1,1,1-trichloroethane with anhydrous hydrofluoric acid in the presence of antimony pentachloride in a solvent (1) which is capable of dissolving antimony pentachloride and 1,1,1-trichloroethane (2) which has a boiling point not lower than 0° C and a melting point not higher than 60° C and (3) which is substantially chemically inert.

We have found that when the reaction of methylchloroform with anhydrous hydrofluoric acid in the presence of antimony pentachloride is effected in a solvent such as 1,1,2-trichloro-1,2,2-trifluoroethane, trichloromethane (i.e., chloroform) to produce F-142$b$ and/or F-143$a$, the solvent used hardly underdoes any chemical change through the course of the reaction and a desired ratio of F-142$b$ to F-143$a$ can be obtained by a given feed ratio of anhydrous hydrofluoric acid to methylchloroform. It has been also found that when F-142$b$ is intended to be produced in major proportion, only very small amount of anhydrous hydrofluoric acid accompanies the F-142$b$ product which is taken out from the reaction system. It is also found that no anhydrous hydrofluoric acid separates as a liquid phase from the reaction system, especially when the starting materials are continuously fed into a solution of antimony pentachloride in the above-mentioned solvent and the resulting products are continuously withdrawn from the reaction system.

It is an object of the present invention to provide a process for preparing 1-chloro-1,1-difluoroethane and/or 1,1,1-trifluoroethane in which the ratio of 1-chloro-1,1-difluoroethane to 1,1,1-trifluoroethane can be varied at will.

It is another object of the present invention to provide a feasible continuous process for preparing 1-chloro-1,1-difluoroethane and/or 1,1,1-trifluoroethane.

It is a further object of the present invention to provide a process for preparing a product containing a major proportion of 1-chloro-1,1-difluoroethane and only a very small amount of anhydrous hydrofluoric acid.

Other objects, features and advantages of the invention will become apparent from the detailed description of preferred embodiments which follows, when considered in light of the accompanying drawing.

BRIEF DESCRIPTION OF THE DRAWING

The single FIGURE is a schematic diagram illustrating a preferred embodiment of a continuous process in accordance with the present invention.

DETAILED DESCRIPTION OF THE INVENTION

It is essential that the solvent used in the process of the invention have
(a) the capability of dissolving both antimony pentachloride and 1,1,1-trichloroethane,
(b) a boiling point not lower than 0° C and a melting point not higher than 60° C, and
(c) substantially chemical inertness.

The term "substantially chemical inertness" of the solvent as used herein means that, under reaction conditions which will be described hereinafter, (1) a reaction between antimony pentachloride and the solvent hardly takes place, i.e., the solvent neither reduces antimony pentachloride to a corresponding trivalent antimony compound, nor hydrolyzes antimony pentachloride nor produces a solid complex with antimony pentachloride, (2) the solvent is less reactive with anhydrous hydrofluoric acid than methylchloroform or 1,1-dichloro-1-fluoroethane, and (3) the solvent does not react with methylchloroform.

The reasons why the solvents used in the present process should satisfy the above requirements are as follows. With regard to the item (a), it is essential to form a homogeneous phase containing the solvent, antimony pentachloride and methylchloroform in order to allow the fluorination reaction to proceed smoothly. As for item (b), the reason why the melting point should be in the range below 60° C is because the solvent must be kept liquid under reaction conditions and the reason why the boiling point of solvent is defined in the range above 0° C is because the use of such solvent ensures easy separation of F-142b and/or F-143a, particularly F-142b, by distillation. With regard to the item (c), a solvent which does not meet the requirement (c) will lower the catalytic activity of antimony pentachloride, and a solvent which is more reactive with anhydrous hydrofluoric acid than methylchloroform will hinder the desired reaction.

Examples of usable solvents are halogenated hydrocarbons, particularly, chlorohydrocarbons and chlorofluorohydrocarbons, containing from 1 to 4 carbon atoms each carbon atom having from 0 to 2, preferably from 0 to 1, hydrogen atoms. (In the above, the term halogen means fluorine, chlorine and bromine.) Representative examples of the solvents include carbon tetrachloride, chloroform, methylene chloride, trichlorofluoromethane, dichloromonofluoromethane, monochloromonofluoromethane, 1,1,2,2-tetrachloro-1,2-difluoroethane, 1,1,1,2-tetrachloro-2,2-difluoroethane, 1,1,2-trichloro-1,2,2-trifluoroethane, 1,1,1-trichloro-2,2,2-trifluoroethane, 1,2-dichloro-1,2-difluoroethane, 1,1-dichloro-2,2-difluoroethane, 1,1,1,2-tetrachloro-1-fluoroethane, 1,1,2,2-tetrachloro-1-fluoroethane, 1,1,2-trichloro-1,2-difluoroethane, 1,1,2-trichloro-2,2-difluoroethane, 1,1,1-trichloro-2,2-difluoroethane, 1,2-dichloro-1,1,2-trifluoroethane, 1,1-dichloro-1,2,2-trifluoroethane, 1,1-dichloro-2,2,2-trifluoroethane, 1,2-dichloro-1,1,2,2-tetrafluoroethane, 1,1-dichloro-1,2,2,2-tetrafluoroethane, pentachloroethane, 1,2-dicloroethane, 1,1,2-trichloroethane, 1,1,2,2-tetrachloroethane, 1,2-dichloro-1,2,3,3,4,4-hexafluorocyclobutane, 1-chloro-1,2,2,3,3,4,4-heptafluorocyclobutane, 2,3-dichloro-1,1,1,4,4,4-hexafluoro-2-butene, 1,2-dibromo-1,1,2,2-tetrafluoroethane, 1,1,1-trifluoro-2-chloro-2-bromoethane, 1,2-dibromo-1,1,2-trifluoro-2-chloroethane and the like. These compounds may be used singly or in combinations of two or more.

Fluorination of methylchloroform is preferably carried out by providing in a reactor a solution of antimony pentachloride catalyst in the solvent, feeding into the solvent anhydrous hydrofluoric acid and methylchloroform and introducing the gas emitted from the reactor into a separation zone preferably a distillation column provided with a condenser. In this case, the content of antimony pentachloride in the solution is preferably 1 to 60% based on the total moles of the solvent and the antimony pentachloride (when calculated on the basis of the formula weight of $SbCl_5$ as one mole). A smaller concentration of antimony pentachloride results in a considerably lower conversion of anhydrous hydrofluoric acid. While conversion of anhydrous hydrofluoric acid becomes higher with a higher concentration, a concentration higher than 60 mol % is disadvantageous due to an increased amount of by-products. More preferably, the concentration of antimony pentachloride is in the range of from 2 to 30 mol %.

The feed ratio of anhydrous hydrogen fluoric acid to methylchloroform is preferably in the range of 1.8 – 3.5 mols of anhydrous hydrofluoric acid per mol of methylchloroform. A smaller ratio tends to increase formation of 1,1-dichloro-1-fluoroethane and is unsuitable for efficiently producing F-142b and/or F-143a. On the contrary, if higher than 3.5 mols, anhydrous hydrofluoric acid will remain unreacted, resulting in a loss of anhydrous hydrofluoric acid.

The reaction temperature suitable for carrying out the process of the invention is generally in the range of from 0° to 80° C, preferably from 10° to 65° C. While the conversion of anhydrous hydrofluoric acid (i.e., a ratio of charged HF to discharged HCl) increases with a rise of the reaction temperature, a reaction temperature above 80° C considerably increases the amount of formation of by-products. A temperature lower than 0° C gives only low conversion of anhydrous hydrofluoric acid, which is not suitable for industrial production.

The reaction pressure is not critical. It depends on the reaction temperature and the composition of the reaction system, and, particularly in case of continuous production, it depends on the composition of the gas in and temperature of the condenser. Generally, the reaction pressure is a pressure in the range of from 0 to 5 $kg/cm^2G$.

The process of the invention can be carried out in a batch, semi-continuous or fully continuous manner. In any case, providing with a distillation column and/or condenser above a reactor is preferred. By this, the gas which is emitted overhead from the reactor and which includes F-142b and/or F-143a, methylchloroform, 1,1-dichloro-1-fluoroethane, hydrogen chloride, anhydrous hydrofluoric acid and solvent is introduced into the distillation column and/or condenser, wherein the F-142b and/or F-143a can be selectively withdrawn out of the system while methylchloroform, 1,1-dichloro-1-fluoroethane and the solvent are returned into the reactor. Selection of a suitable cooling temperature for the condenser would be in the level of ordinary skill.

In accordance with the process of the invention, the F-142b to F-143a formation ratio can be changed arbitrarily in the range of from 0.01 to 5 by properly controlling the feed ratio of anhydrous hydrofluoric acid to methylchloroform. The conversion of anhydrous hydrofluoric acid reaches above 80% and may reach above 90% particularly when F-142b is mainly produced. Under best reaction conditions, the conversion of anhydrous hydrofluoric acid may reach as high as 98%.

The process of the invention does not require any mechanical agitator and thus is very advantageous in simplifying the reaction apparatus and as well as reaction procedures. Upon handling substances which show a strong corrosive tendency, e.g., anhydrous hydrofluoric acid, it has often been experienced that the seal around an agitator produces some trouble. The process of the invention is free from such trouble.

It would seem that the advantages attained by the process of the invention are attributed to the presence of the solvent which serves to bring anhydrous hydrofluoric acid into reaction with methylchloroform or 1,1-dichloro-1-fluoroethane to immediately produce the desired products in a ratio depending on the feed ratio of the hydrofluoric acid to methylchloroform. Though anhydrous hydrochloric acid is hardly soluble in the solvent, it is considered that the solvent serves to effectively diffuse the acid to bring it into contact with the other reactants.

The following example will further illustrate the process of the present invention.

EXAMPLE

An apparatus arranged as shown in FIG. 1 was used for the production of F-142b and/or F-143a.

In the FIGURE, there is shown a reactor designated 4 having a jacket 41 for containing a heat transfer medium, by which the temperature of the materials in the reactor 4 is appropriately controlled. Designated at 1 and 2 are pipes for feeding methylchloroform and anhydrous hydrofluoric acid, respectively, both of which join to a pipe 3 which leads to the bottom of the reactor 4. A pipe 5 is connected to the top of the reactor 4, through which gases generated from a reaction mixture (R) are fed into a distillation column 6. The distillation column 6 is provided with a pipe 7 at the top thereof and a pipe 8 at the bottom thereof, through which low boiling point substances and high boiling point substances are fed to a condenser 9 and the bottom of the reaction vessel 4, respectively. The condenser 9 has pipes 11 and 10 at the top and bottom thereof, respectively, through which a vapor and a condensate are discharged respectively. The vapor is fed successively through a water-containing washing tower 12, an aqueous alkali solution-containing washing tower 14, a dryer 16 and a pipe 17 to a trap (not shown). The condensate is fed back to the upper portion of the distillation column 6 through the pipe 10.

A number of experiments under different reaction conditions as shown in the following Table were conducted in this example. In the example, a 300 ml stainless steel vessel (designated as A in the Table) or a 3 l stainless steel vessel (designated as B in the Table) was used as a reactor. Then, a solution of antimony pentachloride in an amount shown in the Table in a solvent of an amount shown in the Table was placed in the vessel A or B, into which methylchloroform and anhydrous hydrofluoric acid were continuously fed through the pipes 1 and 2 at feed rates shown in the Table, respectively. The experiments were conducted at such reaction temperatures (i.e., the inside temperature of the reaction vessel), reaction pressures (i.e., the inside pressure of the vessel) and condenser temperatures as shown in the Table. The results are also shown in the Table.

The condenser gas composition shown in the Table was determined by a gas chromatography analysis of a gas exhausted from the pipe 17 (at a steady state attained 2 hours after commencement of the reaction). The HF conversion was calculated from the results of analyses of chlorine and fluorine ions in the washing towers 12 and 14.

The experiments 1 - 13 were conducted using different kinds of solvents, experiments 14 - 17 using different concentrations of antimony pentachloride, experiments 18 - 21 at different reaction temperatures, and experiments 22 - 24 in different feed or charging ratios of anhydrous hydrogen fluoric acid/methylchloroform.

|  | Experiment No. |  | 1 | 2 | 3 | 4 |
|---|---|---|---|---|---|---|
|  | reaction vessel |  | A | A | A | A |
|  | solvent |  | $CHCl_3$ | $CF_2ClCFCl_2$ | $CFCl_2CFCl_2$ | $CH_2ClCCl_3$ |
|  | amount of solvent (mol) |  | 0.92 | 0.92 | 0.39 | 0.62 |
|  | amount of $SbCl_5$ (mol) |  | 0.47 | 0.47 | 0.38 | 0.20 |
|  | concentration of $SbCl_5$ (mol %) |  | 33.8 | 33.8 | 49.4 | 29.2 |
| Reaction Conditions | charging rate (mol/hr) | $CH_3CCl_3$ | 0.67 | 0.67 | 0.67 | 0.67 |
|  |  | HF | 1.59 | 1.42 | 1.82 | 1.46 |
|  | charging mol ratio HF/$CH_3CCl_3$ |  | 2.37 | 2.12 | 2.72 | 2.18 |
|  | reaction temperature (° C) |  | 28 | 27 | 29 | 29 |
|  | reaction pressure (kg/cm²G) |  | 0.0 | 0.0 | 0.0 | 0.0 |
|  | condenser temperature (° C) |  | −30 | −30 | −30 | −30 |
| Results | gas composition at condenser outlet (mol %) | $CH_3CF_3$ | 26.8 | 7.9 | 60.3 | 15.6 |
|  |  | $CH_3CF_2Cl$ | 75.5 | 91.9 | 33.4 | 81.1 |
|  |  | $CH_3CFCl_2$ | 0.7 | 0.2 | 6.3 | 3.3 |
|  | HF conversion (%) |  | 98 | 98 | 93 | 98 |
|  | Experiment |  |  |  |  |  |

-continued

| | No. | | 5 | 6 | 7 | 8 |
|---|---|---|---|---|---|---|
| Reaction Conditions | reaction vessel | | A | B | A | A |
| | solvent | | $CH_2Cl_2$ | $CF_2ClCF_2Cl$ | $CFCl_3$ | $CHFCl_2$ |
| | amount of solvent (mol) | | 2.91 | 29.3 | 0.92 | 0.92 |
| | amount of $SbCl_5$ (mol) | | 0.06 | 0.58 | 0.47 | 0.47 |
| | concentration of $SbCl_5$ (mol %) | | 2.0 | 1.9 | 33.8 | 33.8 |
| | charging rate (mol/hr) | $CH_3CCl_3$ | 0.67 | 7.5 | 0.67 | 0.67 |
| | | HF | 1.53 | 17.3 | 1.47 | 1.49 |
| | charging mol ratio $HF/CH_3CCl_3$ | | 2.28 | 2.31 | 2.19 | 2.22 |
| | reaction temperature (° C) | | 24 | 20 | 25 | 25 |
| | reaction pressure (kg/cm²G) | | 0.0 | 1.0 | 0.0 | 0.5 |
| | condenser temperature (° C) | | −20 | −33 | −30 | −30 |
| Results | gas composition at condenser outlet (mol %) | $CH_3CF_3$ | 6.5 | 10.6 | 15.4 | 18.2 |
| | | $CH_3CF_2Cl$ | 92.2 | 89.4 | 84.0 | 80.9 |
| | | $CH_3CFCl_2$ | 1.3 | 0.0 | 0.6 | 0.9 |
| | HF conversion (%) | | 90 | 91 | 97 | 98 |

| | Experiment No. | | 9 | 10 | 11 | 12 |
|---|---|---|---|---|---|---|
| Reaction Conditions | reaction vessel | | A | A | A | A |
| | solvent | | $CH_2ClCH_2Cl$ | $CHCl_2CCl_3$ | $CHCl_2CHCl_2$ | $CF_2ClCCl_2CF_2Cl$ |
| | amount of solvent (mol) | | 0.92 | 0.92 | 0.92 | 0.92 |
| | amount of $SbCl_5$ (mol) | | 0.47 | 0.47 | 0.47 | 0.47 |
| | concentration of $SbCl_5$ (mol %) | | 33.8 | 33.8 | 33.8 | 33.8 |
| | charging rate (mol/hr) | $CH_3CCl_3$ | 0.67 | 0.67 | 0.67 | 0.67 |
| | | HF | 1.75 | 1.45 | 1.45 | 1.61 |
| | charging mol ratio $HF/CH_3CCl_3$ | | 2.61 | 2.16 | 2.16 | 2.41 |
| | reaction temperature (° C) | | 29 | 28 | 28 | 28 |
| | reaction pressure (kg/cm²G) | | 0.0 | 0.0 | 0.0 | 0.0 |
| | condenser temperature (° C) | | −30 | −30 | −30 | −30 |
| Results | gas composition at condenser outlet (mol %) | $CH_3CF_3$ | 41.5 | 9.0 | 12.8 | 32.9 |
| | | $CH_3CF_2Cl$ | 58.1 | 90.2 | 86.6 | 66.8 |
| | | $CH_3CFCl_2$ | 0.4 | 0.8 | 0.6 | 0.3 |
| | HF conversion (%) | | 92 | 93 | 98 | 96 |

| | Experiment No. | | 13 | 14 | 15 | 16 |
|---|---|---|---|---|---|---|
| Reaction Conditions | reaction vessel | | A | A | A | B |
| | solvent | | $CF_3CCl=CClCF_3$ | $CF_2ClCFCl_2$ | $CF_2ClCFCl_2$ | $CF_2ClCFCl_2$ |
| | amount of solvent (mol) | | 0.92 | 0.76 | 0.60 | 18.5 |
| | amount of $SbCl_5$ (mol) | | 0.47 | 0.83 | 0.20 | 1.15 |
| | concentration of $SbCl_5$ (mol %) | | 33.8 | 52.2 | 25.0 | 5.9 |
| | charging rate (mol/hr) | $CH_3CCl_3$ | 0.67 | 0.76 | 0.67 | 15.0 |
| | | HF | 1.90 | 2.32 | 1.52 | 32.0 |
| | charging mol ratio $HF/CH_3CCl_3$ | | 2.84 | 3.05 | 2.27 | 2.18 |
| | reaction temperature (° C) | | 30 | 28 | 25 | 25 |
| | reaction pressure (kg/cm²G) | | 0.0 | 0.0 | 0.0 | 0.3 |
| | condenser temperature (° C) | | −30 | −30 | −30 | −30 |
| Results | gas composition at condenser | $CH_3CF_3$ | 61.2 | 82.6 | 20.7 | 4.6 |
| | | $CH_3CF_2Cl$ | 38.7 | 17.1 | 78.7 | 95.1 |

-continued

| | | | | | | |
|---|---|---|---|---|---|---|
| | outlet (mol %) | CH$_3$CFCl$_2$ | 0.1 | 0.3 | 0.6 | 0.3 |
| | HF conversion (%) | | 92 | 93 | 97 | 96 |
| | Experiment No. | | 17 | 18 | 19 | 20 |
| Reaction Conditions | reaction vessel | | A | A | B | A |
| | solvent | | CF$_2$ClCFCl$_2$ | CF$_2$ClCFCl$_2$ | CF$_2$ClCFCl$_2$ | CF$_2$ClCFCl$_2$ |
| | amount of solvent (mol) | | 1.76 | 1.75 | 18.5 | 1.75 |
| | amount of SbCl$_5$ (mol) | | 0.02 | 0.06 | 0.58 | 0.06 |
| | concentration of SbCl$_5$ (mol %) | | 1.1 | 3.3 | 3.0 | 3.3 |
| | charging rate (mol/hr) | CH$_3$CCl$_3$ | 0.67 | 0.67 | 7.50 | 0.67 |
| | | HF | 1.64 | 1.58 | 16.1 | 1.41 |
| | charging mol ratio HF/CH$_3$CCl$_3$ | | 2.45 | 2.28 | 2.14 | 2.10 |
| | reaction temperature (° C) | | 24 | 5 | 25 | 37 |
| | reaction pressure (kg/cm$^2$G) | | 0.0 | 0.0 | 0.3 | 0.0 |
| | condenser temperature (° C) | | −30 | −30 | −35 | −30 |
| Results | gas composition at condenser outlet (mol %) | CH$_3$CF$_3$ | 1.0 | 5.5 | 3.4 | 2.6 |
| | | CH$_3$CF$_2$Cl | 98.6 | 94.2 | 96.5 | 96.7 |
| | | CH$_3$CFCl$_2$ | 0.4 | 0.3 | 0.1 | 0.7 |
| | HF conversion (%) | | 82 | 90 | 95 | 96 |
| | Experiment No. | | 21 | 22 | 23 | 24 |
| Reaction Conditions | reaction vessel | | B | B | B | B |
| | solvent | | CF$_2$ClCFCl$_2$ | CF$_2$ClCFCl$_2$ | CF$_2$ClCFCl$_2$ | CF$_2$ClCFCl$_2$ |
| | amount of solvent (mol) | | 18.5 | 18.5 | 18.5 | 18.5 |
| | amount of SbCl$_5$ (mol) | | 1.15 | 0.58 | 0.58 | 0.58 |
| | concentration of SbCl$_5$ (mol %) | | 5.9 | 3.0 | 3.0 | 3.0 |
| | charging rate (mol/hr) | CH$_3$CCl$_3$ | 15.0 | 7.50 | 7.50 | 7.50 |
| | | HF | 31.1 | 15.4 | 17.3 | 23.3 |
| | charging mol ratio HF/CH$_3$CCl$_3$ | | 2.07 | 2.05 | 2.41 | 3.11 |
| | reaction temperature (° C) | | 65 | 50 | 50 | 50 |
| | reaction pressure (kg/cm$^2$G) | | 1.0 | 1.0 | 1.0 | 1.0 |
| | condenser temperature (° C) | | −23 | −25 | −25 | −25 |
| Results | gas composition at condenser outlet (mol %) | CH$_3$CF$_3$ | 5.2 | 0.9 | 32.2 | 80.4 |
| | | CH$_3$CF$_2$Cl | 90.3 | 99.1 | 67.8 | 19.6 |
| | | CH$_3$CFCl$_2$ | 4.1 | 0.0 | 0.0 | 0.0 |
| | HF conversion (%) | | 97 | 98 | 96 | 90 |

What is claimed is:

1. A process for the fluorination of 1,1,1-trichloroethane comprising reacting 1,1,1-trichloroethane with anhydrous hydrofluoric acid in the presence of antimony pentachloride catalyst in a solvent which meets the following criteria:
   a. said solvent being capable of dissolving both antimony pentachloride and 1,1,1-trichloroethane;
   b. said solvent having a boiling point of at least 0° C and a melting point not higher than 60° C;
   c. said solvent neither reduces antimony pentachloride to a corresponding trivalent antimony compound, nor hydrolyzes antimony pentachloride nor produces a solid complex with antimony pentachloride;
   d. said solvent being less reactive with anhydrous hydrofluoric acid than methylchloroform or 1,1-dichloro-1-fluoroethane; and
   e. said solvent being non-reactive with methylchloroform.

2. The process as defined in claim 1, wherein said solvent is at least one halogenated hydrocarbon having 1 to 4 carbon atoms, said carbon atoms each having 0 to 2 hydrogen atoms.

3. The process as defined in claim 2, wherein said halogenated hydrocarbon is selected from the group consisting of carbon tetrachloride, chloroform, methylene chloride, trichlorofluoromethane, dichloromonofluoromethane, monochloromonofluoromethane, 1,1,2,2-tetrachloro-2,2-difluoroethane, 1,1,2-trichloro-1,2,2-trifluoroethane, 1,1,1-trichloro-2,2,2-trifluoroethane, 1,2-dichloro-1,2-difluoroethane, 1,1-dichloro-2,2- difluoroethane, 1,1,1,2-tetrachloro-1-fluoroethane, 1,1,2,2-tetrachloro-1-fluoroethane, 1,1,2-trichloro-1,2-difluoroethane, 1,1,2-trichloro-2,2-difluoroethane, 1,1,1-trichloro-2,2-difluoroethane, 1,2-dichloro-1,1,2-trifluoroethane, 1,1-dichloro-1,2,2-trifluoroethane, 1,1-dichloro-2,2,2-trifluoroethane, 1,2-dichloro-1,1,2,2-tetrafluoroethane, 1,1-dichloro-1,2,2,2-tetrafluoroethane, pentachloroethane, 1,2-dichloroethane, 1,1,2-trichloroethane, 1,1,2,2-tetrachloroethane, 1,2-dichloro-1,2,3,3,4,4-hexafluorocyclobutane, 1-chloro-1,2,2,3,3,4,4-heptafluorocyclobutane, 2,3-dichloro-1,1,1,4,4,4-hexafluoro-2-butene, 1,2-dibromo-1,1,2,2-tetrafluoroethane, 1,1,1-trifluoro-2-chloro-2-bromoethane, 1,2-dibromo-1,1,2-trifluoro-2-chloroethane, 1,1,2,2-tetrachloro-1,2-difluoroethane, 1,1,1,2-tetrachloroethane and 1,2,2,3-tetrachloro-1,1,3,3-tetrafluoropropane.

4. The process as defined in claim 1, wherein said solvent is at least one hydrocarbon selected from the group consisting of chloroform, 1,1,2-trichloro-1,2,2-trifluoroethane, 1,1,2,2-tetrachloro-1,2-difluoroethane, 1,1,1,2-tetrachloroethane, methylene chloride, 1,2-dichloro-1,1,2,2-tetrafluoroethane, trichlorofluoromethane, dichlorofluoromethane, 1,2-dichloroethane, pentachloroethane, 1,1,2,2-tetrachloroethane, 1,2,2,3-tetrachloro-1,1,3,3-tetrafluoropropane, 2,3-dichloro-1,1,1,4,4,4-hexafluoro-2-butene.

5. The process as defined in claim 1, wherein said catalyst is used in an amount of between 1 and 60% based on the total moles of said catalyst and said solvent.

6. The process as defined in claim 1, wherein the mole ratio of anhydrous hydrofluoric acid to 1,1,1-trichloroethane ranges from 1.8 to 3.5.

7. The process as defined in claim 1, wherein said reaction is performed at a temperature of between 0° C. and 80° C.

8. The process as defined in claim 1, which comprises providing in a reactor a solution of said catalyst in said solvent, bringing simultaneously both anhydrous hydrofluoric acid and 1,1,1-trichloroethane into direct contact with said solution, and recovering a product comprising at least one component selected from 1-chloro-1,1-difluoroethane and 1,1,1-trifluoroethane from the gas emitted from the reactor.

9. The process as defined in claim 8, wherein the content of said catalyst in the solution ranges from 1 to 60% based on the total moles of said catalyst and said solvent.

10. The process as defined in claim 8, wherein the mole ratio of anhydrous hydrofluoric acid to 1,1,1-trichloroethane ranges from 1.8 to 3.5.

11. The process as defined in claim 8, wherein said contacting is by feeding a mixture of anhydrous hydrofluoric acid and 1,1,1-trichloroethane into said solution in the reactor.

12. The process as defined in claim 8, wherein said recovering step comprises introducing said gas into a first separation zone to separate said gas into a lower boiling point phase and a higher boiling point phase and recovering said product from said lower boiling point phase.

13. The process as defined in claim 12, wherein said recovering of said product from said lower boiling point phase comprises introducing said lower boiling point phase into a second separation zone to separate said lower boiling point phase into a condensed liquid phase and a gas phase and recovering said product from said gas phase.

14. The process as defined in claim 12, further comprising recycling said higher boiling point phase into the reactor.

15. The process as defined in claim 13, further comprising recycling said condensed liquid phase into the first separation zone.

* * * * *